(12) United States Patent
Robb et al.

(10) Patent No.: US 11,015,253 B2
(45) Date of Patent: *May 25, 2021

(54) SURFACE TREATMENT PROCESS FOR IMPLANTS MADE OF TITANIUM ALLOY

(71) Applicant: BIOMET 3I, LLC, Palm Beach Gardens, FL (US)

(72) Inventors: T. Tait Robb, Stewart, FL (US); Bruce Berckmans, III, Palm Beach Gardens, FL (US); Ross W Towse, San Marcos, CA (US); Robert L Mayfield, Jupiter, FL (US)

(73) Assignee: BIOMET 3I, LLC, Palm Beach Gardens, FL (US)

(*) Notice: Subject to any disclaimer, the term of this patent is extended or adjusted under 35 U.S.C. 154(b) by 41 days.

This patent is subject to a terminal disclaimer.

(21) Appl. No.: 16/257,910

(22) Filed: Jan. 25, 2019

(65) Prior Publication Data

US 2019/0292666 A1 Sep. 26, 2019

Related U.S. Application Data

(63) Continuation of application No. 13/558,037, filed on Jul. 25, 2012, now Pat. No. 10,227,697, which is a
(Continued)

(51) Int. Cl.
*C23F 1/26* (2006.01)
*A61L 27/06* (2006.01)
(Continued)

(52) U.S. Cl.
CPC ............. *C23F 1/26* (2013.01); *A61L 27/06* (2013.01); *A61L 27/50* (2013.01);
(Continued)

(58) Field of Classification Search
CPC .. C23F 1/26; A61L 27/06; A61L 27/50; A61L 2400/18; Y10T 29/49567;
(Continued)

(56) References Cited

U.S. PATENT DOCUMENTS 3,022,783 A 2/1962 Tucker et al.
3,605,123 A 9/1971 Hahn
(Continued)

FOREIGN PATENT DOCUMENTS

AT 328067 B 3/1976
CA 926552 A 5/1973
(Continued)

OTHER PUBLICATIONS

"U.S. Appl. No. 09/237,605, Appeal Decision mailed May 30, 2007", 16 pgs.
(Continued)

*Primary Examiner* — Duy Vu N Deo
(74) *Attorney, Agent, or Firm* — Schwegman Lundberg & Woessner, P.A.

(57) ABSTRACT

A titanium 6 Al/4V alloy is provided with a surface topography that is similar to the Osseotite® surface produced on commercially pure titanium. Native oxide is removed from the Ti 6Al/4V alloy, followed by contacting the metal at ambient temperature with an aqueous hydrochloric acid solution containing a relatively small amount of hydrofluoric acid.

9 Claims, 13 Drawing Sheets

Related U.S. Application Data continuation of application No. 10/843,916, filed on May 12, 2004, now Pat. No. 8,251,700.

(60) Provisional application No. 60/471,463, filed on May 16, 2003.

(51) Int. Cl.
  *A61L 27/50* (2006.01)
  *A61C 8/00* (2006.01)
  *A61F 2/30* (2006.01)

(52) U.S. Cl.
  CPC ..... *A61C 2008/0046* (2013.01); *A61F 2/3094* (2013.01); *A61F 2/30767* (2013.01); *A61F 2/30771* (2013.01); *A61F 2002/30925* (2013.01); *A61F 2310/00023* (2013.01); *A61L 2400/18* (2013.01); *Y10T 29/49567* (2015.01)

(58) Field of Classification Search
  CPC .......... A61C 2008/0046; A61C 8/0015; A61F 2/30767; A61F 2/30771; A61F 2/3094; A61F 2002/30925; A61F 2310/00023
  USPC ...................................................... 216/102
  See application file for complete search history.

(56) References Cited

U.S. PATENT DOCUMENTS

| | | | |
|---|---|---|---|
| 3,767,437 A | 10/1973 | Cruz, Jr. et al. | |
| 3,790,507 A | 2/1974 | Hodosh | |
| 3,855,638 A | 12/1974 | Pilliar | |
| 3,919,723 A | 11/1975 | Heimke et al. | |
| 3,986,212 A | 10/1976 | Sauer | |
| 3,987,499 A | 10/1976 | Scharbach et al. | |
| 4,011,602 A | 3/1977 | Rybicki et al. | |
| 4,051,598 A | 10/1977 | Sneer | |
| 4,145,764 A | 3/1979 | Suzuki et al. | |
| 4,146,936 A | 4/1979 | Aoyagi et al. | |
| 4,180,910 A | 1/1980 | Straumann et al. | |
| 4,195,409 A | 4/1980 | Child | |
| 4,199,864 A | 4/1980 | Ashman | |
| 4,223,412 A | 9/1980 | Aoyagi et al. | |
| 4,261,350 A | 4/1981 | Branemark et al. | |
| 4,330,891 A | 5/1982 | Branemark et al. | |
| 4,336,618 A | 6/1982 | Raab | |
| 4,366,183 A | 12/1982 | Ghommidh et al. | |
| 4,406,761 A | 9/1983 | Shimogori et al. | |
| 4,530,116 A | 7/1985 | Frey | |
| 4,547,157 A | 10/1985 | Driskell | |
| 4,547,327 A | 10/1985 | Bruins et al. | |
| 4,608,052 A | 8/1986 | Van Kampen et al. | |
| 4,629,464 A | 12/1986 | Susumu et al. | |
| 4,654,314 A | 3/1987 | Takagi et al. | |
| 4,687,675 A | 8/1987 | Nakano et al. | |
| 4,693,986 A | 9/1987 | Vit et al. | |
| 4,702,930 A | 10/1987 | Heide et al. | |
| 4,704,126 A | 11/1987 | Baswell et al. | |
| 4,722,688 A | 2/1988 | Lonca | |
| 4,746,532 A | 5/1988 | Suzuki et al. | |
| 4,818,559 A | 4/1989 | Hama et al. | |
| 4,826,434 A | 5/1989 | Krueger et al. | |
| 4,839,215 A | 6/1989 | Starling et al. | |
| 4,861,733 A | 8/1989 | White | |
| 4,865,603 A | 9/1989 | Noiles | |
| 4,871,578 A | 10/1989 | Adam | |
| 4,874,434 A | 10/1989 | Riggs, Jr. et al. | |
| 4,878,914 A | 11/1989 | Miwa et al. | |
| 4,882,196 A | 11/1989 | Shimamune et al. | |
| 4,908,030 A | 3/1990 | Linkow et al. | |
| 4,911,953 A | 3/1990 | Hosonuma et al. | |
| 4,919,751 A | 4/1990 | Sumita et al. | |
| 4,932,868 A | 6/1990 | Linkow et al. | |
| 4,938,938 A | 7/1990 | Ewers et al. | |
| 4,944,754 A | 7/1990 | Linkow et al. | |
| 4,960,646 A | 10/1990 | Shimamune et al. | |
| 4,963,145 A | 10/1990 | Takagi et al. | |
| 4,969,906 A | 11/1990 | Kronman | |
| 4,988,299 A | 1/1991 | Branemark | |
| 5,000,685 A | 3/1991 | Brajnovic | |
| 5,030,096 A | 7/1991 | Hurson et al. | |
| 5,032,552 A | 7/1991 | Nonami et al. | |
| 5,034,352 A | 7/1991 | Vit et al. | |
| 5,039,546 A | 8/1991 | Chung et al. | |
| 5,071,351 A | 12/1991 | Green, Jr. et al. | |
| 5,108,399 A | 4/1992 | Eitenmuller et al. | |
| 5,141,576 A | 8/1992 | Shimamune et al. | |
| 5,180,564 A | 1/1993 | Wahl et al. | |
| 5,188,800 A | 2/1993 | Green et al. | |
| 5,190,795 A | 3/1993 | Culler | |
| 5,195,891 A | 3/1993 | Sulc | |
| 5,199,873 A | 4/1993 | Schulte et al. | |
| 5,205,745 A | 4/1993 | Kamiya et al. | |
| 5,205,921 A | 4/1993 | Shirkanzadeh | |
| 5,219,361 A | 6/1993 | Von Recum et al. | |
| 5,222,983 A | 6/1993 | Schmitz et al. | |
| 5,242,706 A | 9/1993 | Cotell et al. | |
| 5,258,030 A | 11/1993 | Wolfarth et al. | |
| 5,263,986 A | 11/1993 | Noiles et al. | |
| 5,279,831 A | 1/1994 | Constantz et al. | |
| 5,297,963 A | 3/1994 | Dafatry | |
| 5,306,305 A | 4/1994 | Lee | |
| 5,310,464 A | 5/1994 | Redepenning | |
| 5,316,476 A | 5/1994 | Krauser | |
| 5,316,477 A | 5/1994 | Calderon | |
| 5,324,199 A | 6/1994 | Branemark | |
| 5,344,425 A | 9/1994 | Sawyer | |
| 5,344,457 A | 9/1994 | Pilliar et al. | |
| 5,360,448 A | 11/1994 | Thramann | |
| 5,362,237 A | 11/1994 | Chalifoux | |
| 5,366,374 A | 11/1994 | Vlassis | |
| 5,368,480 A | 11/1994 | Balfour et al. | |
| 5,368,483 A | 11/1994 | Sutter | |
| 5,399,090 A | 3/1995 | Padros-Fradera | |
| 5,405,436 A | 4/1995 | Maurer et al. | |
| 5,427,754 A | 6/1995 | Nagata et al. | |
| 5,433,606 A | 7/1995 | Niznick et al. | |
| 5,441,536 A | 8/1995 | Aoki et al. | |
| 5,456,723 A | 10/1995 | Steinemann | |
| 5,472,734 A | 12/1995 | Perrotta et al. | |
| 5,478,237 A | 12/1995 | Ishizawa | |
| 5,484,286 A | 1/1996 | Hansson | |
| 5,489,210 A | 2/1996 | Hanosh | |
| 5,496,399 A | 3/1996 | Ison et al. | |
| 5,503,558 A | 4/1996 | Clokie | |
| 5,543,019 A | 8/1996 | Lee et al. | |
| 5,564,923 A | 10/1996 | Grassi et al. | |
| 5,571,017 A | 11/1996 | Niznick | |
| 5,571,188 A | 11/1996 | Ellingsen | |
| 5,573,401 A | 11/1996 | Davidson et al. | |
| 5,588,838 A | 12/1996 | Hansson et al. | |
| 5,591,029 A | 1/1997 | Zuest | |
| 5,603,338 A | 2/1997 | Beaty | |
| 5,607,480 A | 3/1997 | Beaty | |
| 5,639,237 A | 6/1997 | Fontenot | |
| 5,816,811 A | 10/1998 | Beaty | |
| 5,863,201 A | 1/1999 | Lazzara et al. | |
| 5,876,453 A | 3/1999 | Beaty | |
| 5,989,027 A | 11/1999 | Wagner et al. | |
| 6,069,295 A | 5/2000 | Leitao | |
| 6,183,255 B1 | 2/2001 | Oshida | |
| 6,491,723 B1 | 12/2002 | Beaty | |
| 6,652,765 B1 | 11/2003 | Beaty | |
| 6,702,855 B1 | 3/2004 | Steinemann et al. | |
| 8,251,700 B2 * | 8/2012 | Robb | A61L 27/06 433/173 |
| 10,227,697 B2 * | 3/2019 | Robb | A61L 27/06 |
| 2003/0135282 A1 | 7/2003 | Anitua | |
| 2012/0288828 A1 | 11/2012 | Robb et al. | |

FOREIGN PATENT DOCUMENTS

| | | |
|---|---|---|
| CH | 679117 A5 | 12/1991 |
| DE | 2313678 A1 | 10/1974 |

(56) References Cited

FOREIGN PATENT DOCUMENTS

| | | | |
|---|---|---|---|
| DE | 2717615 A1 | 10/1978 | |
| EP | 202031 A2 | 11/1986 | |
| EP | 212929 A2 | 3/1987 | |
| EP | 0213836 A2 | 11/1987 | |
| EP | 0409810 A2 | 1/1991 | |
| EP | 455929 A1 | 11/1991 | |
| EP | 606566 A1 | 7/1994 | |
| EP | 0806211 B1 | 10/2002 | |
| EP | 0987031 B1 | 4/2003 | |
| EP | 1150620 B1 | 11/2003 | |
| FR | 2289160 A2 | 5/1976 | |
| FR | 2421595 A1 | 11/1979 | |
| GB | 834256 A | 5/1960 | |
| GB | 2045083 A | 10/1980 | |
| GB | 2252501 A | 8/1992 | |
| JP | 63147455 A | 6/1988 | |
| JP | 1148254 A2 | 6/1989 | |
| JP | 3146679 A2 | 6/1991 | |
| JP | 6234559 A | 8/1994 | |
| SE | 332486 A | 11/1971 | |
| WO | WO-9205745 A1 | 4/1992 | |
| WO | WO-9413334 A1 | 6/1994 | |
| WO | WO-9616611 A1 | 6/1996 | |
| WO | WO-0156628 A1 | 8/2001 | |

OTHER PUBLICATIONS

"U.S. Appl. No. 09/237,605, Decision on Pre-Appeal Brief mailed Jul. 30, 2007", 13 pgs.

"U.S. Appl. No. 09/237,605, Decision on Pre-Appeal Brief mailed Nov. 13, 2007", 15 pgs.

"U.S. Appl. No. 13/558,037, Advisory Action dated Feb. 21, 2014", 3 pgs.

"U.S. Appl. No. 13/558,037, Advisory Action dated Jul. 24, 2014", 2 pgs.

"U.S. Appl. No. 13/558,037, Advisory Action dated Dec. 12, 2013", 5 pgs.

"U.S. Appl. No. 13/558,037, Appeal Brief filed Feb. 28, 2014", 19 pgs.

"U.S. Appl. No. 13/558,037, Appeal Decision dated Dec. 15, 2016", 12 pgs.

"U.S. Appl. No. 13/558,037, Examiner Answer to Appeal Brief mailed Jul. 30, 2014", 13 pgs.

"U.S. Appl. No. 13/558,037, Examiner Interview Summary dated Nov. 15, 2013", 3 pgs.

"U.S. Appl. No. 13/558,037, Final Office Action dated Jul. 13, 2018", 12 pgs.

"U.S. Appl. No. 13/558,037, Final Office Action dated Jul. 31, 2013", 13 pgs.

"U.S. Appl. No. 13/558,037, Non Final Office Action dated May 18, 2017", 8 pgs.

"U.S. Appl. No. 13/558,037, Non Final Office Action dated Nov. 29, 2017", 10 pgs.

"U.S. Appl. No. 13/558,037, Non Final Office Action dated Dec. 14, 2012", 10 pgs.

"U.S. Appl. No. 13/558,037, Notice of Allowance dated Oct. 19, 2018", 5 pgs.

"U.S. Appl. No. 13/558,037, Preliminary Amendment filed Jul. 25, 2012", 7 pgs.

"U.S. Appl. No. 13/558,037, Reply Brief filed Sep. 30, 2014", 14 pgs.

"U.S. Appl. No. 13/558,037, Response filed Feb. 15, 2017 to Appeal Decision mailed Dec. 15, 2016", 8 pgs.

"U.S. Appl. No. 13/558,037, Response filed Feb. 28, 2017 to Non Final Office Action dated Nov. 29, 2017", 10 pgs.

"U.S. Appl. No. 13/558,037, Response filed Apr. 15, 2013 to Non Final Office Action dated Dec. 14, 2012", 9 pgs.

"U.S. Appl. No. 13/558,037, Response filed Aug. 18, 2017 to Non Final Office Action dated May 18, 2017", 10 pgs.

"U.S. Appl. No. 13/558,037, Response filed Sep. 13, 2018 to Final Office Action dated Jul. 13, 2018", 7 pgs.

"U.S. Appl. No. 13/558,037, Response filed Oct. 31, 2013 to Final Office Action dated Jul. 31, 2013", 16 pgs.

"U.S. Appl. No. 13/558,037, Response filed Dec. 30, 2013 to Advisory Action dated Dec. 12, 2013", 5 pgs.

"Bone response to surface modified titanium implants-studies on the tissue response after I year to machined and electropolished implants with different oxide thicknesses", Journal of Materials Science Materials in Medicine, (1997), 721-729.

"Canadian Application Serial No. 2,467,320, Office Action dated Jun. 19, 2008", 2 pgs.

"Denar Introduces Steri-Oss: The First Complete Oral Rehabilitation Implant System,", (May 2004), 10 pgs.

"European Application Serial No. 04011563.6, Office Action dated May 23, 2008", 29 pgs.

"European Application Serial No. 04011563.6, Office Action dated Jun. 18, 2008", 1 pg.

"Micro focus (Ref. D50)", (May 2004).

"Micro focus (Ref. D5I)", (May 2004).

"Orale Implantologie", (Ref. D58),, (May 2004), 2 pgs.

"Paragon Technology Report", (Oct. 1997), 2-11.

"Price List", Friatec,, (Oct. 1998), 40 pgs.

"Price List and Catalog", Friadent, (Sep. 2000), 35 pgs.

"Product Literature for Frialit®-2 Implant System,", Friadent, (Feb. 1999), 12 pgs.

"Product Literature for Frialit®-2 Implant System,", Interpore International and Friatec,, (1996), 3 pgs.

"Product Literature for Frialite-2,", Friadent, (2000), 2 pgs.

"Product Literature for Frialit®-2, Abridged Directions for Use,", Interpore International and Friatec,, (1996,1997), 20 pgs.

"Standard Practice for Surface Preparation and Marking of Metallic Surgical Implants", ASTM Designation F 86-84,, (May 2004), 3 pgs.

"Standard Recommended Practice for Descaling and Cleaning Titanium and Titanium Alloy Surfaces", (Ref.D6),, (May 2004), 465-467.

"Step-Screw Implant", Dental Products Report,, (Mar. 1993), 1 pg.

"Strauman Literature Abstracts,", (May 2004), 8 pgs.

"Strauman SLA: Reducing healing time further,", (May 2004), 6 pgs.

"The Influence of Implant Surface on Hard- and Soft Tissue Integration Friatec website,", (Jun. 6, 1998), 11 pgs.

"Titan", (Ref. D35),, (May 2004), 4 pgs.

Adell, et al., "Tissue-Integrated Prostheses", Per-Ingvar Branemark, (Ref. 43), (May 2004), 19 pgs.

Albrektsson, et al., "Effect of a Glycoprotein Monomolecular Layer on the Integration of Titanium Implants in Bone (Ref. D48)", (May 2004), 4 pgs.

Albrektsson, T, et al., "Osseo integrated Titanium Implants", (May 2004.), 155-170.

Baier, R E, et al., "Implant Surface Preparation", International Journal of Oral & Maxillofacial Implants, vol. 3,, (1988), 24 pgs.

Baier, R E, et al., "Surface Energetics and Biological Adhesion", International Symposium on Physicochemical Aspects of Polymer Surfaces, vol. 2,, (May 2004), 895-909.

Binon, P, "Evaluation of Machining Accuracy and Consistency of Selected Implants, Standard", International Journal of Prosthodontics, vol. 8,, (1995), 18 pgs.

Bowers, K, et al., "Optimization of Surface Micromorphology for Enhanced Osteoblast Responses In Vitro,", International Journal of Oral & Maxillofacial Implants, vol. 7, No. 3,, (1992), 302-310.

Boyan, et al., "Titanium Surface Roughness Alters Responsiveness ofMG63 Osteoblast-Like Cells to la,25-(0H)2D3", J Miomed Mater Res, 39, (1998), 77-85.

Branemark, P I, et al., "Osseointegrated Implants in the Treatment of the Edentulous Jaw Experience From A I 0 Year Period,", Stockholm, Almqvist & Wiksell International, (1977), 3 pgs.

Buser, et al., "Interface Shear Strength of Titanium Implants With a Sandblasted and Acid-Etched Surface: A Biomechanical Study in the Maxilla of Miniature Pigs,", J Biomed Mater Res, 45, (1999), 75-83.

(56) References Cited

OTHER PUBLICATIONS

Buser, D, et al., "Influence of Surface Characteristics on Bone Integration of Titanium Implants, A Histomorphometric Study in Miniature Pigs", Journal of Biomedical Materials Research, vol. 25, (1991), 14 pgs.
Buser, Daniel, et al., "Removal Torque Values of Titanium Implants in the Maxilla of Miniature Pigs", (May 2004.), 611-619.
Carlsson, L, et al., "Removal Torques for Polished and Rough Titanium Implants", International Journal of Oral & Maxillofacial Implants, vol. 3 (1988), 21-24.
Claes, L., et al., "The Dependence of the Removal Torque of a Leg Screw Surface and implantation Time (Ref. D30),", (May 2004), 5 pgs.
Cochran, et al., "Bone Response to Unloaded and Loaded Titanium Implants With a Sandblasted and Acid-Etched Surface: A Histometric Study in the Canine Mandible", J Biomed Mater Res, 40, (1998), 1-11.
Cochran, et al., "Evaluation of an Endosseous Titanium Implant With a Sandblasted and Acid-Etched Surface in the Canine Mandible: Radiographic Results,", Clinical Oral Implants Research 1996: 7:, 240-252.
Cook, Stephen D., et al., "Fatigue properties of carbon- and porous-coated Ti-6AI-4V alloy", Journal of Biomedical Materials Research, vol. 18, 497-512, (1984), 16 pgs.
Cook, Stephen D., et al., "Interface Mechanics and Histology of Titanium and Hydroxylapatite-Coated Titanium for Dental Implant Applications", (Ref. 47),, (May 2004), 15-22.
Curtis, A. S. G, et al., "The Effects of Topographic and Mechanical Properties of Materials on Cell Behavior", Critical Reviews in Biocompatibility, vol. 5, Issue 4,, (1990), 343-362.
De Groot, K., et al., "Plasma Sprayed Coatings of Hydroxylapatite", Journal of Biomedical Materials Research, vol. 21, (1987), 1375-1381.
Eberhardt, A, et al., "Effects of Precoating Surface Treatments on Fatigue OfTi-6Al-4V,", Journal of Applied Biomaterials, vol. 6 (1995), 171-174.
Gomez-Roman, German, et al., "The Frialit-2 Implant System: Five-Year Clinical Experience in Single-Tooth and Immediately Postextraction Applications,", The International Journal of Oral & Maxillofacial Implants, vol. 12, No. 3, (1997), 299-309.
Gotfredsen, K, et al., "Histomorphometric and Removal Torque Analysis for TiO2-Blasted Titanium Implants", Clinical Oral Impl. Res, (Feb. 6, 1992), 77-84.
Henry, Patrick J., et al., "Comparative Surface Analysis of Two Osseointegrated Implant Systems", (Ref. D 19), (May 2004), 23-27.
Johansson, C., et al., "Removal Forces for Osseo integrated Titanium Implants", Implant Materials in Biofunction,(Ref. 31), (May 2004), 87-92.
Karagianes, M. T., "Porous Metals As a Hard Tissue Substitute", Biomat. Med. Dev., Art. Org.,vol. 1, No. 1, (1973), 4 pgs.
Kasemo, Bengt, et al., "Metal Selection and Surface Characteristics", Tissue-Integrated Prostheses Osseointegration in Clinical Dentistry (Quintessence Books), 99-116, (1985), 20 pgs.
Kiesweiter, et al., "Surface Roughness Modulates the Local Production of Growth Factors and Cytokines by Osteoblast-Like MG-63 Cells", Journal of Biomedical Materials Research, vol. 32,, (1996), 55-63.
Klokkevold, P, et al., "Evaluation of a New Chemically Enhanced Implant Surface by Torque Removal Tests in the Rabbit Femur,", Clinical Oral Implants Research, (1997), 2 pgs.
Larsson, et al., "Bone response to surface modified titanium implants: studies on electropolished implants", Bio Materials vol. 15, No. 13,, (1994), 1062-1074.
Larsson, et al., "Bone response to surface-modified titanium implants: studies on the early tissue response to machined and electropolished implants with different oxide thicknesses",, Bio Materials vol. 17, No. 6, (1996), 605-616.
Lazzara, R, et al., "Retrospective Multicenter Analysis Of31 Endosseous Dental Implants Placed Over a Five Year Period", Clinical Oral Implants Research, vol. 7,, (1996), 73-83.

Ledermann, "Das Prinzip der neuen Ledermann-Schraube (German Reference D3),", (May 2004), 3 pgs.
Ledermann, et al., "The Ha-TI Implant", Schweiz Monatsschr Zahnmed, vol. I 01, No. 5,, (May 1991), 7 pgs.
Ledermann, Philippe D., et al., "Die Quintessenz", (Ref. 26),, (May 2004), 10 pgs.
Ledermann, Philippe D., et al., "Heute so zuverlassig wie vor 50 Jahren", German (Ref. D4), (May 2004).
Ledermann, Philippe D., et al., "Swiss Dent", (Ref. D25),, (May 2004), 10 pgs.
Martin, et al., "Effect of Titanium Surface Roughness on Proliferation, Differentiation, and Protein Synthesis ofHuman Osteoblast-Like Cells (MG63)", Journal of Biomedical Materials Research, vol. 29,, (1995), 389-402.
Mears, "Materials and Orthopaedic Surgery", (Ref.42),, (May 2004. ), 6 pgs.
Messersmith, P, et al., "Stress Enhancement and Fatigue Susceptibility of Porous Coated Ti-6AI-4V Implants: An Elastic Analysis,", Journal of Biomedical Materials Research, vol. 24,, (1990), 591-604.
Murphy, M W, "Tissue Reaction of Rats and Guinea-Pigs to Co—Cr Implants With Different Surface Finishes", (Ref. D8),, (May 2004), 9 pgs.
Olefjord, Ingemar, et al., "Surface Analysis of Four Dental Implant Systems", International Journal of Oral & Maxillofacial Implants, vol. 8, No. 1, (1993), 18 pgs.
Persson, LG, et al., "Re-Osseointegration After Treatment of Peri-Implantitis at Different Implant Surfaces. An Experimental Study in the Dog", Clin Oral Impl. Res.,12, (2001), 595-603.
Predecki, Paul, et al., "Attachment of Bone to Threaded Implants by Ingrowth and Mechanical Interlocking", Journal of Biomedical Materials Research, vol. 6,, (1972), 401-412.
Roberts, Eugene W, et al., "Osseous adaptation to continuous loading of rigid endosseous implants", (Ref. D7),, (May 2004), 95-111.
Schroeder, A., et al., "Gewebsraktion auf ein Titan-Hohlzylinderimplantat mit Titan-Spritzschichtobernache", vol. 86, No. 7 University of Bern (Switzerland), Clinic for Dental Maintenance (Schweizerisch Monatschrift fiir Zahnheilkunde (Jul. 7, 1976), 713-727.
Schroeder, Andre, et al., "Orale Implantologie (Ref. 36)", (May 2004), 9 pgs.
Schulte, J., "External Hex Manufacturing Tolerances of Six Implant Systems: A Pilot Study", Implant Dentistry,, (1994), 51-53.
Schulte, W, et al., "The First 15 years of the Tuebinger Implant and Its Further Development to the Frialit®-2 System,", Zeitschrift fur Zahnarzliche Implantologie, Band VIII,, (Feb. 1992), 3-22.
Schwartz, et al., "Effect of Titanium Surface Roughness on Chonrocyte Proliferation, Matrix Production, and Differentiation Depends on the State of Cell Maturation,", Journal of Biomedical Materials Research, vol. 30,, (1996), 145-155.
Shults, R R, "A Study of Fatigue Properties of Hydroxylapatite Coated Titanium Alloy Implant Materials", Department of Biomedical Engineering, Memphis State University,, (May 2004), 1 pg.
Smith, Todd, "The Effect of Plasma-Sprayed Coatings on the Fatigue of Titanium Alloy Implants", (Ref.29),, (May 2004), 54-56.
Sorensen, J. A., et al., "Comparison of Interface Fidelity OfImplant Systems", Journal of Dental Research, vol. 70, No. 540, Abstract No. 2191, (1991), 1 pg.
Steflik, David E., et al., "A Comparative Investigation in Dogs: 2-Year Morphometric Results of the Dental Implant-Bone Interface,",, (May 2004), 15-25.
Steflik, David E., et al., "Histomorphometry of the Dental Implant-Bone Interface: One-Year Results of a Comparative Investigation in Dogs",, (May 2004), 501-511.
Steinemann, et al., "Adhesion of Bone to Titanium", (Ref. 27), (May 2004), 4 pgs.
Sullivan, Daniel, et al., "Preliminary Results of a Multicenter Study Evaluating Chemically-Enhanced Pure Titanium Implants", Journal of Prosthetic Dentistry, (1997), 27 pgs.
Sutter, Franz, et al., "The New Restorative Concept of the ITI Dental Implant System: Design and Engineering,", vol. 13, No. 5 (1993), 409-431.

(56) References Cited

OTHER PUBLICATIONS

Swanson, S. A. V., et al., "The Scientific Basis of Joint Replacement", (Ref. D4I), (May 2004), 6 pgs.

Swart, et al., "Short-Term Plasma-Cleaning Treatments Enhance In Vitro Osteoblast Attachment to Titanium,", Journal of Oral Implantology, vol. XVIII, No. 2,, (1992), 130-137.

Thomas, K A, et al., "The Effect of Surface Macro texture and Hydroxylapatite Coating on the Mechanical Strengths and Histologic Profiles of Titanium Implant Materials", Journal of Biomedical Materials Research, vol. 21,, (1987), 1395-1414.

Thomas, Kevin A., et al., "An evaluation of variables influencing implant fixation by direct bone appostion", (Ref. 46), (May 2004.), 875-901.

Weigand, A.J., et al., "Ion-Beam-Sputter Modification of the Surface Morphology of Biological Implants,", J.Vac. Soc. Technol.vol. I4,No. 1, (Jan./Feb. 1977), 326-331.

Weinlaender, M, et al., "Histomorphometry of Bone Apposition Around Three Types of Endosseous Dental Implants", International Journal of Oral & Maxillofacial Implants, vol. 7, No. 4, (1992), 20 pgs.

Wennerberg, et al., "A histomorphometric and removal torque study of screw-shaped titanium implants with three different surface topographies", (Ref. D33), (May 2004), 24-30.

Wennerberg, et al., "An animal study of c.p. titanium screws with different surface topographies", (Ref. D 32), (May 2004), 302-309.

Wennerberg, Ann, et al., "Design and Surface Characteristics of 13 Commercially Available Oral Implant Systems,", Int. J. Oral Maxillofactial Implants,, (1993), 622-633.

Wheeler, K R, et al., "Porous Metals As a Hard Tissue Substitute. Part II. Porous Metal Properties,", Biomat. Med. Dev., Art. Org., vol. I, No. 2,, (1973), 7 pgs.

Wheeler, Stephen L, et al., "Eight Year Clinical Retrospective Study of Titanium Plasma-Sprayed and Hydroxyapatite-Coated Cylinder Implants", International Journal of Oral & Maxillofacial Implants vol. 11, No. 3,, (1996), 340-350.

Widmer, Martin, "Kontrolle der Oberflachenqualitat von anodisierten Titan-Implantaten mittels Reflexionsspektroskopie", (Feb. 1998), 50 pgs.

Wilke, H.-J., et al., "The Influence of Various Titanium Surfaces on the Interface Shear Strength Between Implants and Bone,", Clinical Implant Materials, Advances in Biomaterials, vol. 9,, (1990), 309-314.

Wong, M, et al., "Effect of Surface Topology on the Osseointegration Of Implant Materials in Trabecular Bone", Journal of Biomedical Materials Research, vol. 29,, (1995), 1567-1575.

Yue, S, et al., "The Fatigue Strength of Porous-Coated Ti-6%Al-4% V Implant Alloy,", Journal of Biomedical Materials Research, vol. 18, (1984), 1043-1058.

* cited by examiner

SURFACE TREATMENT PROCESS FOR IMPLANTS MADE OF TITANIUM ALLOY

CROSS-REFERENCE TO RELATED APPLICATION

This application claims priority of provisional patent application 60/471,463, filed May 16, 2003.

FIELD OF THE INVENTION

This invention relates generally to the surface of metal implants, such as those placed in the human body.

BACKGROUND OF THE INVENTION

This invention principally relates to the surface of titanium alloy dental implants, although it has application to other types of implants made of titanium alloys. More specifically, the invention relates to roughened surfaces provided on dental implants to improve the osseointegration of the implant surface with the bone, thereby shortening the time between initial insertion of the implant and the installation of a prosthetic tooth.

Various techniques have been suggested for roughening implants, each producing a unique surface. One approach has been to apply materials to the surface of the implant, for example hydroxyapitite, a material that is considered to improve the bonding of the implant to bone because the hydroxyapitite is chemically related to bone. In a related approach, titanium particles have been sprayed onto a titanium implant to roughen the surface. Anodization to add titanium oxides to the surface has also been proposed. Roughening also can be done by removing some of the surface. Grit blasting with fine particles has been proposed to create dents and to abrade away some of the surface. Another method is the use of acid etching to create a roughened surface. At least one supplier of dental implants has proposed grit blasting to create a coarse roughened surface, followed by acid etching to form a superimposed fine roughening.

Etching the surface of titanium with acids has been included in many processes proposed for manufacturing dental implants. In many cases, only general reference to selecting from a list of mineral acids, in other instances specific acids are used. For example, Toho Titanium Co. disclosed in Japanese Published Patent Application JP3146679A1 a two step treatment in which aqueous hydrofluoric acid was used to etch the surface, followed by a second treatment with a solution hydrofluoric acid and hydrogen peroxide. Another example is found in U.S. Published Application 2003/0135282A1, in which an implant is treated with a sequence of three acids—hydrofluoric, sulfuric and hydrochloric acid. The etched surface is coated with plasma before use to improve integration with bone.

In a series of U.S. patents, including U.S. Pat. Nos. 5,603,338; 5,876,453; 5,863,201; and 6,652,765 assigned to Implant Innovations Inc., a unique two-step acid treatment was disclosed, which is used on dental implants to produce an Osseotite® surface. The first acid treatment uses aqueous hydrofluoric acid to remove the "native oxide", that is, the titanium oxide found on titanium metal surfaces. Removing the native oxide makes the metal surface more accessible to etching by other acids, assuring uniform etching of the titanium surface. Other methods of removing the native oxide could be used, such as plasma treatment, but the initial treatment with aqueous hydrofluoric acid was preferred. The second acid treatment preferably used a mixture of hydrochloric and sulfuric acids to etch the exposed titanium surface. A relatively fine etching was achieved, having peak-to-valley heights of 10 μm or less. The peak-to-peak distance typically is about 1-3 μm. This Osseotite® surface has achieved commercial success, having reduced the time required for osseointegration of the titanium implant with bone.

Previous U.S. patents have shown the titanium surface obtained by scanning electron microscopy (SEM). Another method of describing the surface is surface mapping microscopy (SMM), which produces a computer-generated three-dimensional picture of the region being examined, and several calculated measures of the roughness of the surface. It will be understood by those skilled in the art that acid treatment produces a surface that appears very uniform to the naked eye, but contains variations that become evident only when greatly magnified, as in the photomicrographs. Each region will not be precisely the same as the others, but nevertheless, the variations are small and fall within the general limits discussed above. By carefully controlling the treatment process, each implant has substantially the same surface.

It has more recently been found that, while a consistent response to the two-step acid treatment is obtained on commercially pure titanium, the same treatment process produces non-uniform results on titanium alloys. Because titanium alloys have some benefits over commercially pure titanium, it would be desirable if the topography of the Osseotite® surface were to be duplicated on a titanium alloy surface. To achieve this goal, the inventors found that the process used for commercially pure titanium required unexpected revisions to achieve the desired surface on titanium alloys. Their new process will be described in detail below.

SUMMARY OF THE INVENTION

A process for producing on a titanium alloy a desired surface topography similar to the Osseotite® surface removes the native oxide on the titanium alloy and thereafter, and before the titanium alloy reoxidizes significantly, the surface is etched in an aqueous solution of hydrofluoric and hydrochloric acids to produce the desired surface. The native oxide maybe removed by immersing for about 40 to 60 seconds in an aqueous solution of hydrofluoric acid containing about 7.9 to 9.0 wt % hydrofluoric acid. In a preferred embodiment, the surface is etched for about 19-21 minutes at room temperature in an acid mixture containing from about 0.053 to about 0.105 wt % hydrofluoric (HF) acid and from about 19 to about 21 wt % hydrochloric (HCl) acid. The conditions for both acid treatments are chosen to provide the desired surface topography, while minimizing the loss of titanium metal.

In one specific embodiment, the native oxide is removed by immersing the implant in an 8.45 wt % HF solution at ambient temperature for 45 seconds. After rinsing to remove the residual acid, the implant is immersed for 19.5 minutes at ambient temperature in a 20 wt % HCl solution containing 0.0845 wt % HF.

The conditions for both acid treatments are chosen to provide the desired surface topography, while minimizing the loss of titanium metal.

In one aspect, the invention is a dental implant that has been treated according to the process described above to provide the desired surface topography in predetermined regions of the implant.

DETAILED DESCRIPTION OF THE PREFERRED EMBODIMENTS

Titanium and Titanium Alloys

Although other metals, and ceramics have been proposed for use in dental implants, titanium has been generally used. Particularly commercially pure titanium, which contains trace amounts of carbon, iron, oxygen, hydrogen, and nitrogen. Titanium alloys have also been used since they are stronger than the commercially pure grades of titanium. One commonly used titanium alloy, Ti/6Al/4V, contains 6 wt % aluminum and 4 wt % vanadium, hereafter referred to as Ti 6/4.

A characteristic of titanium and its alloys is the rapid formation of tenacious titanium oxide films on the surface, a feature which contributes to titanium's resistance to corrosion. This oxide film is considered to be a combination of various oxides of titanium, including $TiO$, $TiO_2$, $Ti_2O_3$, and $Ti_3O_4$. It has been referred to the "native oxide" film. Measurement of the native oxide film by Auger spectrometer indicates that it typically has a depth of 70 to 150 Angstroms.

As previously disclosed, removing the native oxide is important if a uniformly roughened surface is to be produced by acid etching. Experience has shown that most acids are not capable of removing the native oxide sufficiently so that a uniform roughness can be produced. Titanium surfaces are often pickled in mixtures of hydrofluoric acid and nitric acids to clean the surface. Aqueous solutions of hydrofluoric acid alone, without the addition of oxidizing acids such as nitric acid, are very aggressive toward titanium and its native oxide film. A relatively brief exposure to a dilute solution of hydrofluoric acid will remove the native oxide. Since after removing the native oxide, the hydrofluoric acid will begin to consume the metal as well, an undesirable result, the titanium implant is removed from the acid and rinsed to stop further attack. However, as is well known, the titanium metal surface will begin to oxidize quickly. Consequently, the exposed metal surface should be protected against oxygen exposure until the titanium implant is immersed in an acid bath to uniformly etch the surface, creating the desired surface topography. Other methods of removing the native oxide could be used, such as plasma treatment, but the use of hydrofluoric acid is preferred.

Figure 1A:
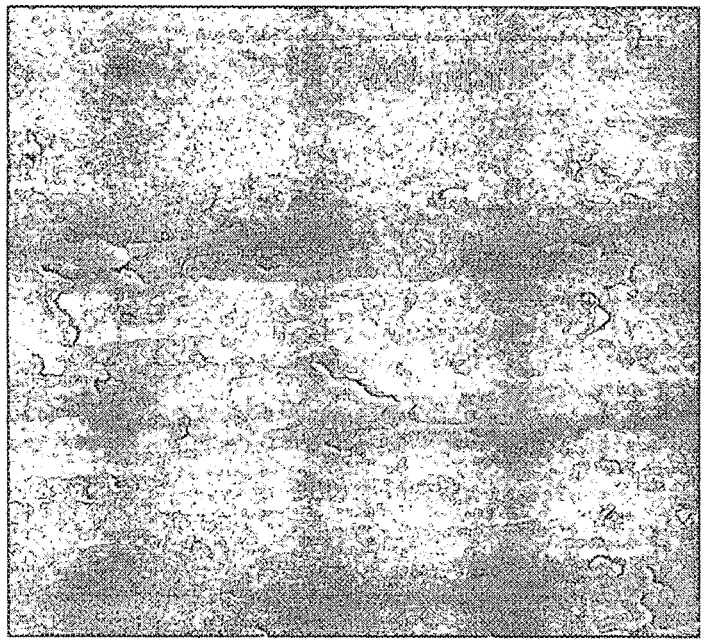
FIG. 1A shows a commercially pure titanium machined surface.
Figure 1B:
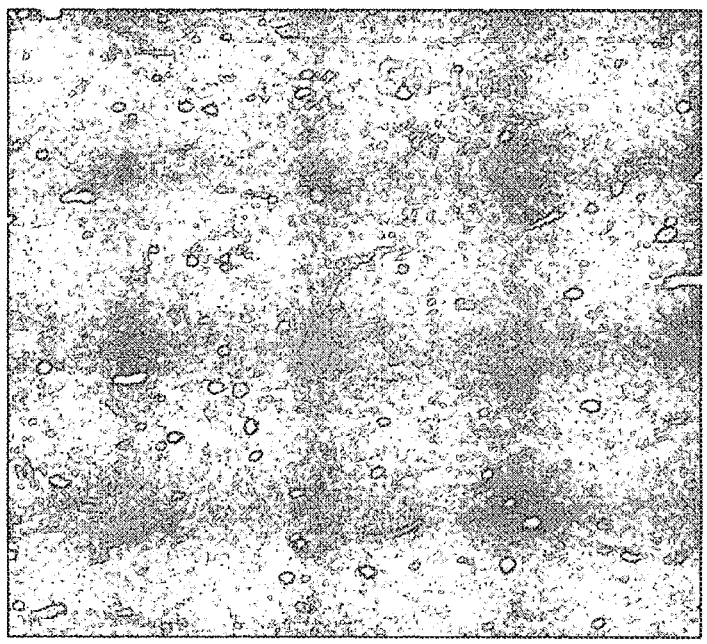
FIG. 1B shows the surface of FIG. 1A after being treated with HF

The rate at which titanium is etched depends on the concentration of the hydrofluoric acid. A hydrofluoric acid solution containing about 15 vol. % of 49 wt % hydrofluoric acid was found to permit complete removal of the native oxide within about one-half minute, but with minimal consumption of the metal. This is illustrated in FIGS. 1A and B which show at 2000× magnification the surface of a commercially pure titanium metal dental implant after machining (producing macro-features such as threads or grooves) and then after being exposed to hydrofluoric acid to remove the native oxide. The machining marks have disappeared and the hydrofluoric acid has left the titanium grains exposed after the native oxide has been removed and some of the grain boundary material has been removed.

Figure 1C:
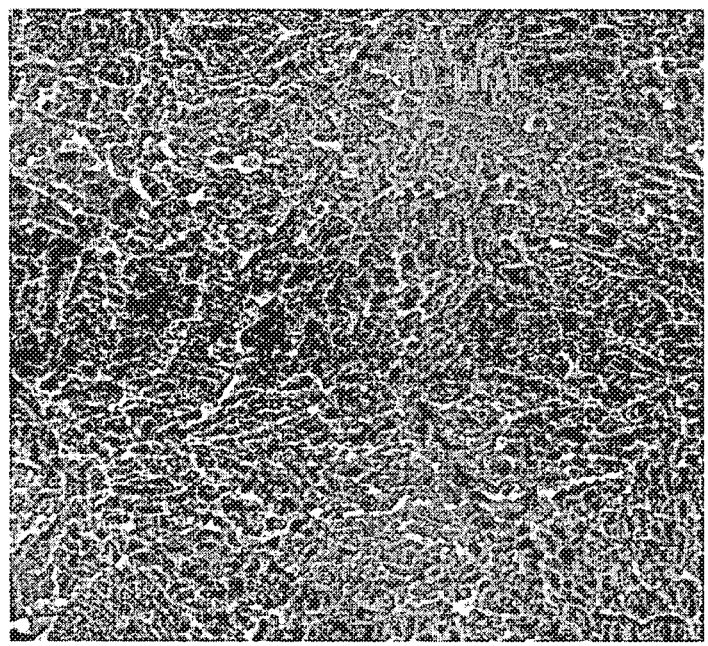
FIG. 1C shows the surface of FIG. 1B after being etched with HCl and H2SO4 so as to produce an Osseotite® surface on pure titanium.
Figure 1D:
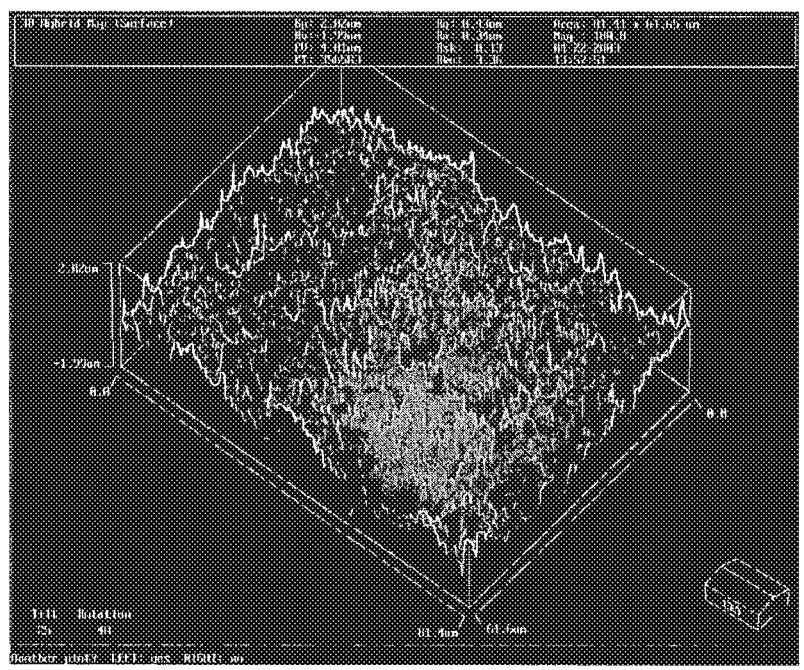
FIG. 1D is a surface map of the Osseotite® surface of FIG. 1C.

In FIG. 1C, the surface of the commercially pure titanium (after native oxide has been removed) has been etched with a solution of 19.55 wt % hydrochloric acid and 72.29 wt % sulfuric acid at 60-70° C. for about 7 minutes. This desirable surface topography has been clinically demonstrated to achieve enhanced osseointegration. Implants having this surface are sold under the Osseotite® trademark by the assignee of the present invention. This desirable surface has a generally uniform set of sharp peaks with a maximum peak-to-valley height of 10 µm or less. The average peak-to-peak distance is about 1-3 µm. The result of a typical examination of an Osseotite® surface by surface mapping microscopy is shown in FIG. 1D.

FIGS. 1A-1D illustrate the process and results produced on a commercially pure titanium dental implant. Clinical success of the Osseotite® surface in improving osseointegration of the implants has been confirmed and it is well accepted in the marketplace. Therefore, the present inventors had expected to create the same surface topography on titanium alloy Ti 6/4 using the same treatment. However, they were surprised to discover that the process providing uniform results on commercially pure titanium failed to produce the characteristic surface topography when applied to Ti 6/4 alloy.

Other etching solutions were tested. In some instances, a surface similar to the Osseotite® surface was obtained, but in other cases, acid etching was ineffective. It was found also that the effect on Ti 6/4 alloy varied from batch to batch, so that each batch had to be tested to determine its suitability. After further investigation of this problem, the inventors found that certain acid etching solutions were capable of consistently producing the desired surface on Ti 6/4 alloy.

Acid Etching of Ti 6/4 Alloy

FIGS. 1E, and 2C-E, 3A-E, 4A, B, and 5A-D illustrate the results of some of the acids tested on Ti 6/4 E.L.I. alloy, as defined by ASTM B348 Grade 23 or ASTM F136. In each case, the implants had been given the same treatment in a hydrofluoric acid solution to remove the native oxide on the surface. In particular, the implants were immersed in 8.45 wt % hydrofluoric acid at room temperature. The results of the etching processes shown in FIGS. 1E, and 2C-E, 3A-E, 4A, B, and 5A-D can be compared with FIG. 1C, the Osseotite® surface produced on commercially pure titanium metal by an acid treatment with an initial mixture of 19.55 wt % hydrochloric acid and 72.29 wt % sulfuric acid at 60-70° C. for 7 minutes.

Experiments were carried out with a series of acid compositions, the results being shown in Figures. The acid compositions and treatment conditions are summarized in the following table.

TABLE 1

| | | Native Oxide Removal Treatment | | Etching Acid Compostion[1] | | | | | |
|---|---|---|---|---|---|---|---|---|---|
| FIG. | Ti: | 8.45 wt % HF | Time, min. | HF | HCl | $H_2SO_4$ | $HNO_3$ | Time min. | Temp °C. |
| 1C | CP | Yes | 1.0 | — | 19.55 | 77.29 | — | 7 | 60-70 |
| 1E | 6/4 | Yes | 1.0 | — | 19.55 | 77.29 | — | 7 | 60-70 |
| 2A | 6/4 | No | — | 0.284 | 1.062 | — | 2.297 | 1 | 61 |
| 2B | 6/4 | No | — | 0.284 | 1.062 | — | 2.297 | 8 | 61 |
| 2C | 6/4 | Yes | 0.5 | 0.284 | 1.062 | — | 2.297 | 0.5 | 61 |
| | | | | — | 19.55 | 77.29 | — | 1.0 | 61 |
| 2D | 6/4 | Yes | 0.5 | 0.284 | 1.062 | — | 2.297 | 0.5 | 61 |
| | | | | — | 19.55 | 77.29 | — | 7 | 61 |
| 2E | 6/4 | Yes | 0.17 | 0.284 | 1.062 | — | 2.297 | 1.5 | 61 |
| | | | | 1.143 | — | — | 1.923 | 1.5 | ambient |
| 3A | 6/4 | Yes | 1.0 | 0.284 | 1.062 | — | 2.297 | 7 | ambient |
| 3B | 6/4 | Yes | 2.5 | 0.284 | 1.062 | — | 2.297 | 7 | ambient |
| 3C | 6/4 | Yes | 1.0 | 0.284 | 1.062 | — | 2.297 | 10 | ambient |
| 3D | 6/4 | Yes | 2.5 | 0.284 | 1.062 | — | 2.297 | 10 | ambient |
| 3E | 6/4 | Yes | 2.5 | 0.284 | 1.062 | — | 2.297 | 10 | ambient |
| 4A | 6/4 | Yes | 1.5 | — | 20 | — | — | 14 | ambient |
| 4B | 6/4 | Yes | 1.5 | — | 20 | — | — | 21 | ambient |
| 5A | 6/4 | Yes | 1.0 | 0.26 | 20 | — | — | 20 | ambient |
| 5B | 6/4 | Yes | 1.0 | 0.175 | 20 | — | — | 20 | ambient |
| 5C | 6/4 | Yes | 1.0 | 0.09 | 20 | — | — | 20 | ambient |
| 5D | 6/4 | Yes | 1.0 | 0.09 | 20 | — | — | 20 | ambient |

[1]wt % acid, remainder water

The above table generally follows the progress of experiments carried out to determine the acid etching needed to produce the desired surface topography on Ti 6/4 alloy. To produce the surface of FIG. 1C, the native oxide on the commercially pure titanium was removed by exposure to an 8.45 wt % HF solution for 1 minute at ambient temperature. After rinsing in deionized water containing baking soda to neutralize the residual acid and a further rinse in deionized water, the titanium was immersed in an aqueous solution of 19.55 wt % HCl and 77.29 wt % $H_2SO_4$ for 7 minutes at 60-70° C. to produce a uniformly roughened surface, i.e. the Osseotite® surface.

Figure 1E:
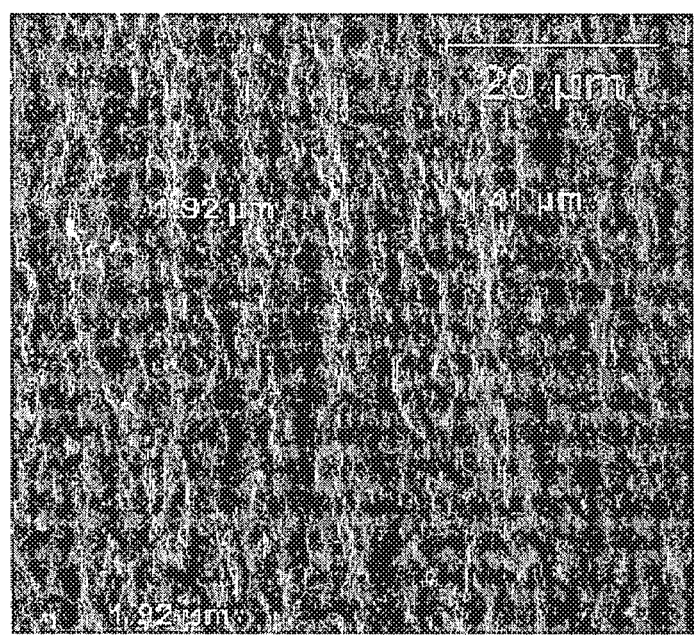
FIG. 1E shows the effect of the treatment of FIG. 1A-C on Ti 6/4 alloy.

FIG. 1E illustrates the surprising result when the same procedure was carried out on Ti 6/4 alloy. As will be seen in the photograph, the characteristic Osseotite surface was not obtained on Ti 6/4 alloy. The machining marks were still visible. It was concluded that a different etching process was needed for use with Ti 6/4 alloy if the Osseotite® surface was to be provided on the Ti 6/4 alloy.

Figure 2A:
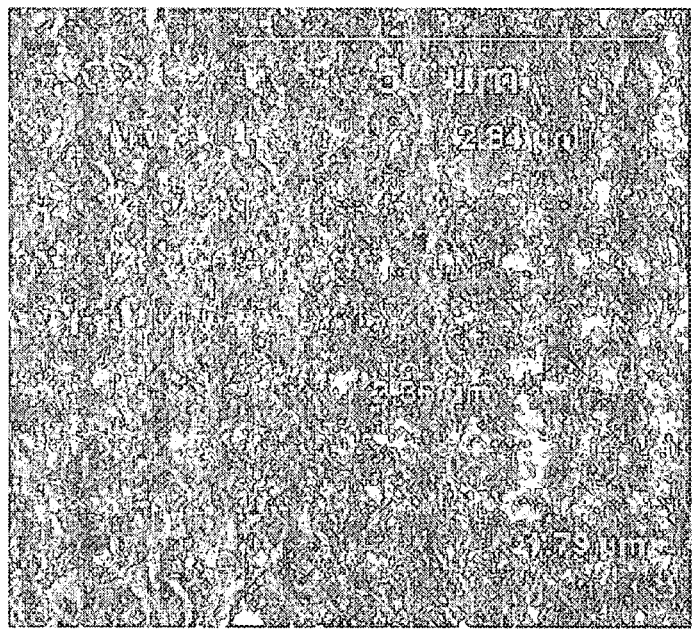
FIG. 2A-E show several etching processes on Ti 6/4 alloy.
Figure 2B:
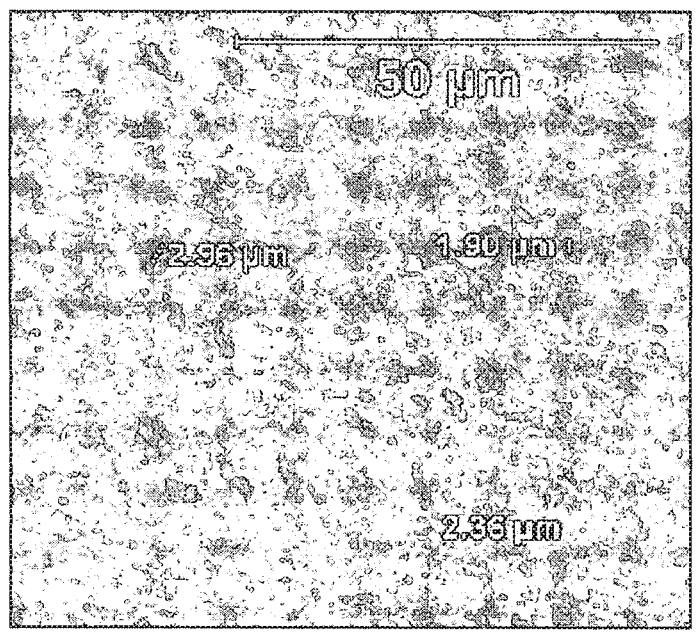

FIGS. 2A-E show the results obtained when two known etching acid mixtures were used. One was Keller's solution, containing $HNO_3$, and HCl, and the second was Kroll's solution, containing HF and $HNO_3$. The compositions used are shown in Table I above. FIGS. 2A and 2B show that Keller's solution alone did not produce the Osseotite surface, although some pitting can be seen. Since the pretreatment with HF solution to remove the native oxide was not done, it is presumed that the native oxide interfered with the attempted etching with Keller's solution.

Figure 2C:
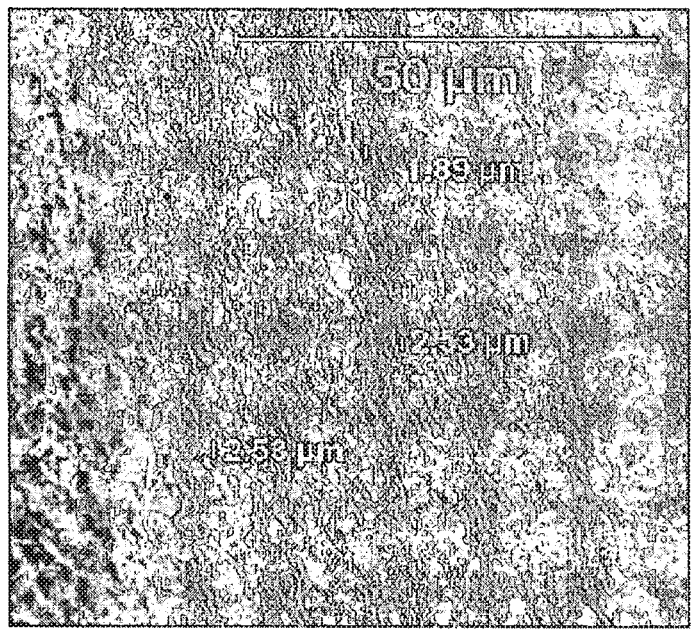
Figure 2D:
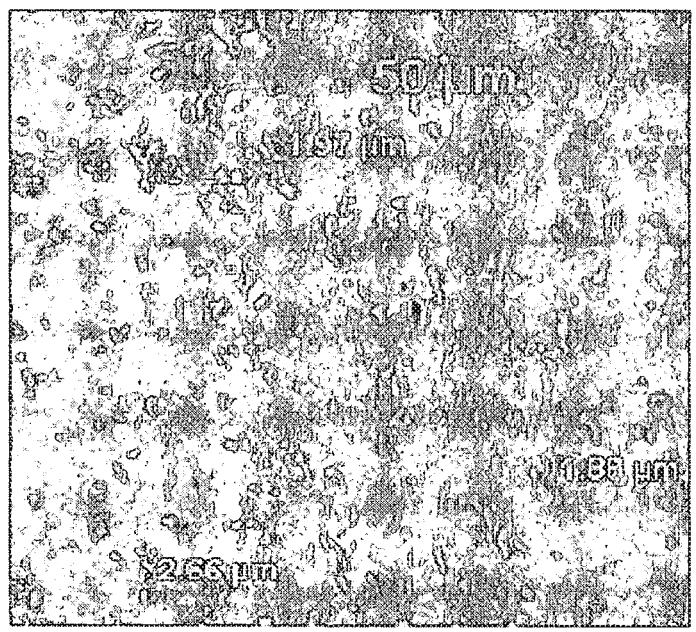
Figure 2E:
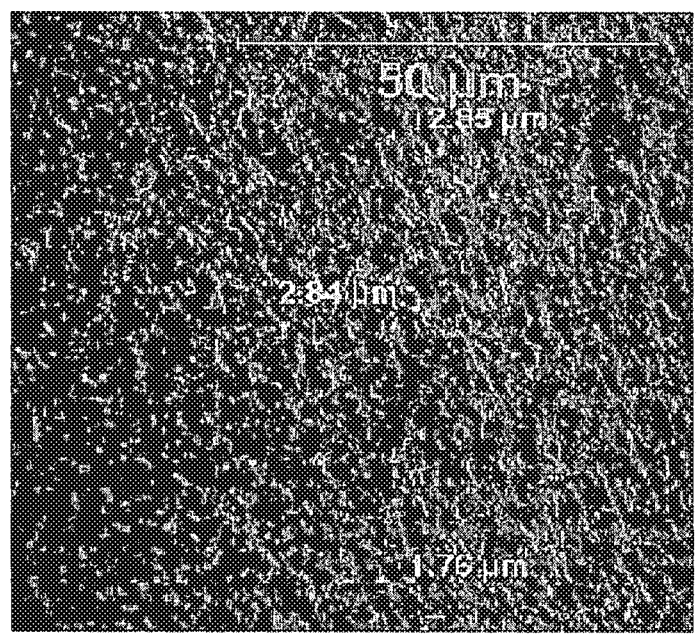
Figure 3A:
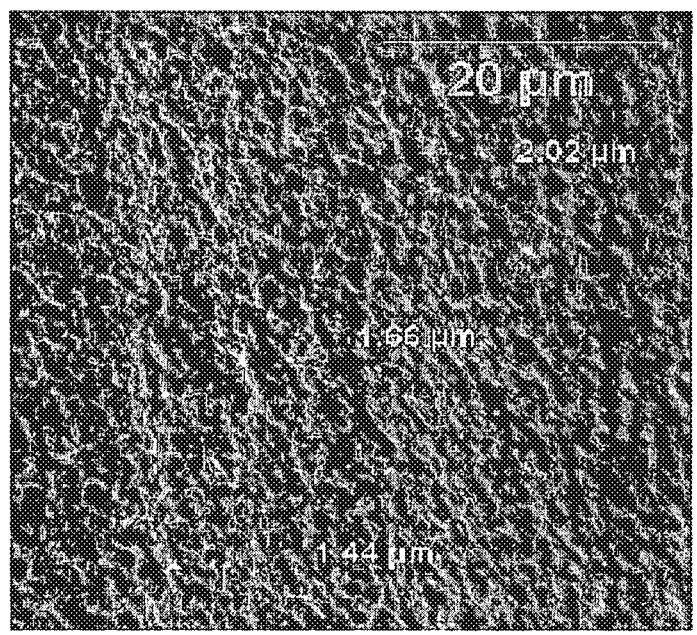
FIG. 3A-E show the effect of etching with Keller's reagent and Kroll's reagent.
Figure 3B:
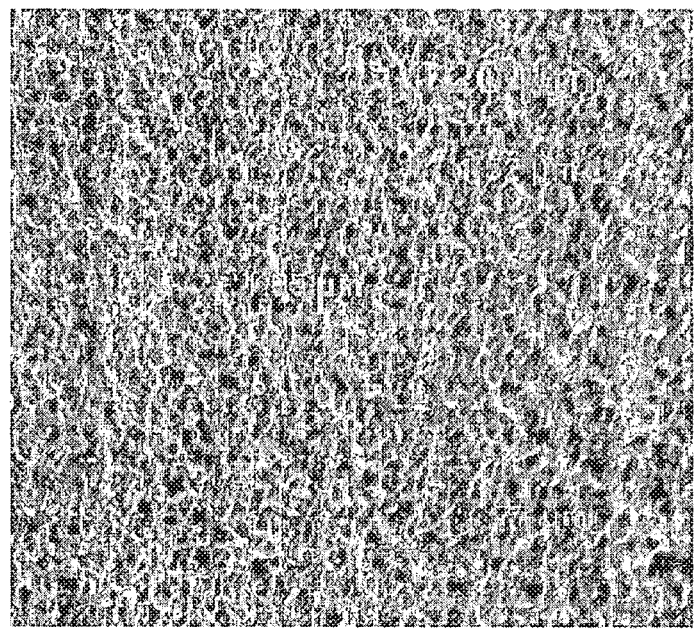
Figure 3C:
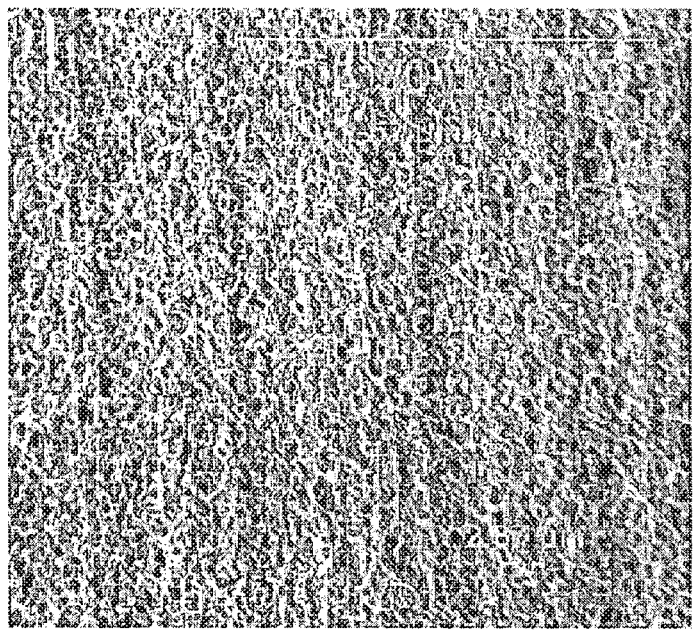
Figure 3D:
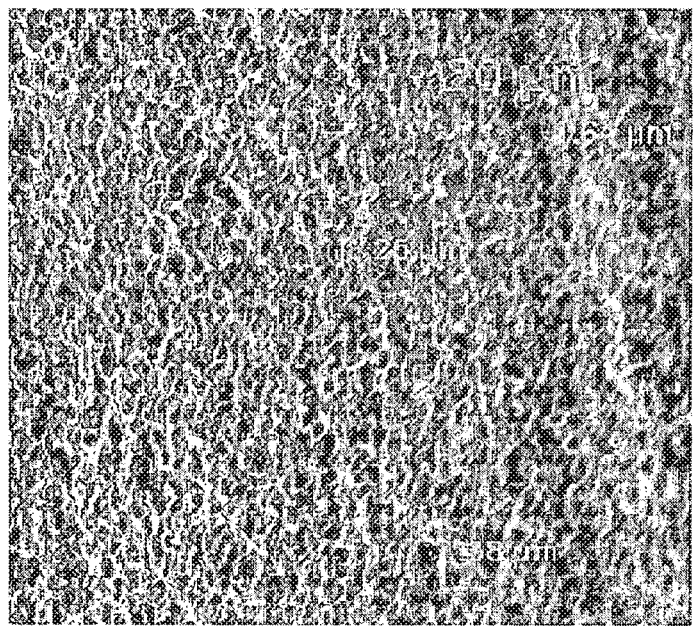
Figure 3E:
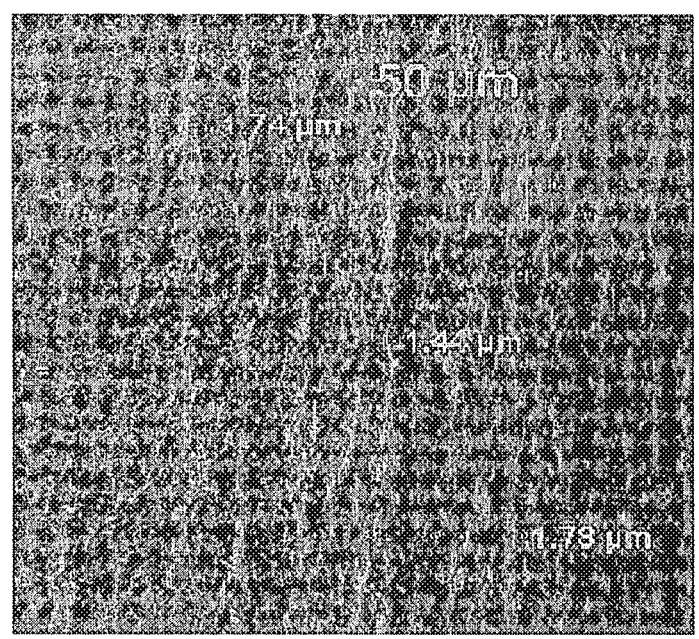

FIGS. 2C to 2E show the results achieved when the native oxide was removed by pre-treatment with an HF solution and thereafter the titanium surface was exposed to two acid solutions in sequence. In FIGS. 2C and 2D, Keller's solution was used, followed by the mixture of HCl and $H_2SO_4$, known to be successful in etching chemically pure titanium. In FIG. 2E, Keller's solution was used first, followed by immersion of the Ti 6/4 alloy in Kroll's solution. None of these tests produced a surface topography like that shown in FIG. 1C on the Ti 6/4 alloy.

FIGS. 3A-3E show the results obtained when the native oxide was removed with an HF solution, and Keller's solution was used for etching, hut at ambient temperature rather than at 61° C. previously used. It was found that this process was capable of providing a surface similar to FIG. 1C on some samples of Ti 6/4 alloy, but not on others (compare FIG. 3 D with FIG. 3 E). The difference in response of the samples appeared to be associated with the machining or the alloy heat (i.e., the conditions associated with a specific batch of titanium alloy). Therefore, additional experimentation was undertaken. However, it was concluded that etching with Keller's solution may be useful also, provided that control of the quality of the Ti 6/4 alloy can be achieved.

Figure 4A:
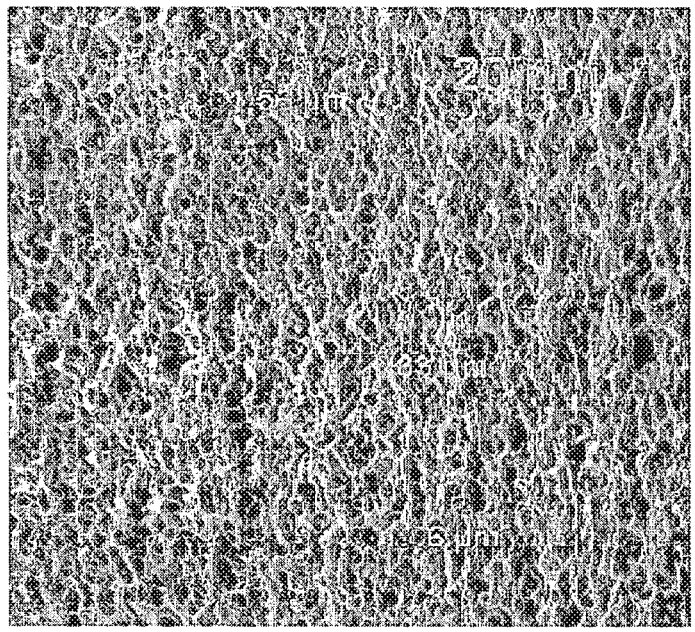
FIG. 4A-B show the effect of etching with HCl alone.
Figure 4B:
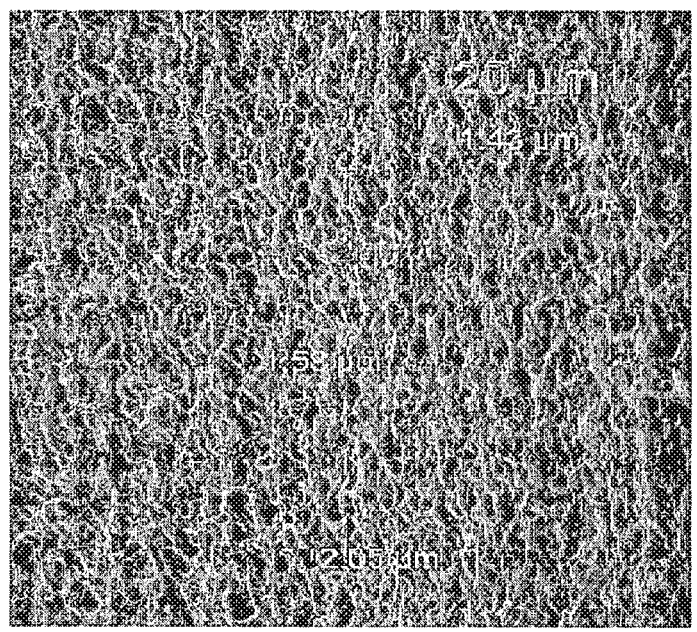
Figure 5A:
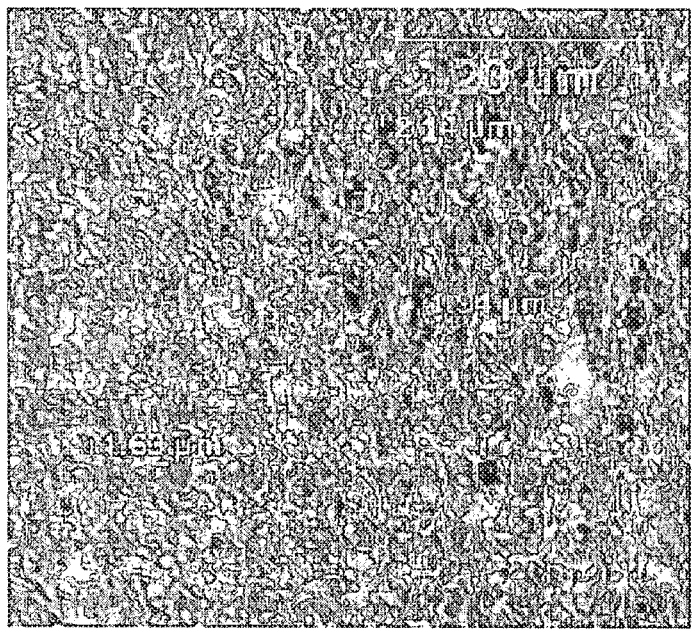
FIG. 5A-D show the effect of etching with HCl plus HF.
Figure 5B:
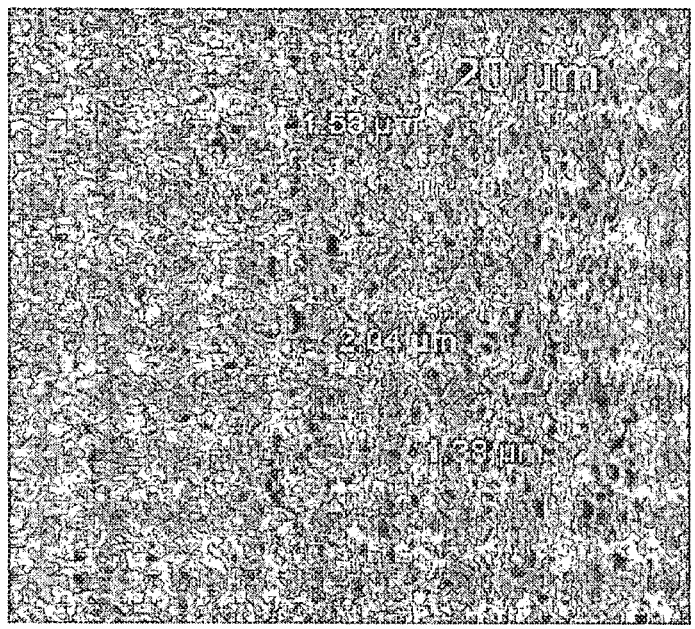
Figure 5C:
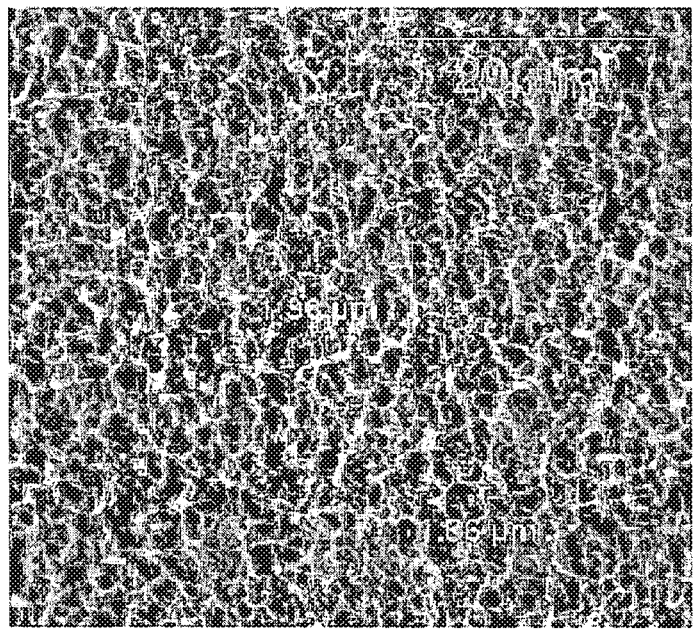
Figure 5D:
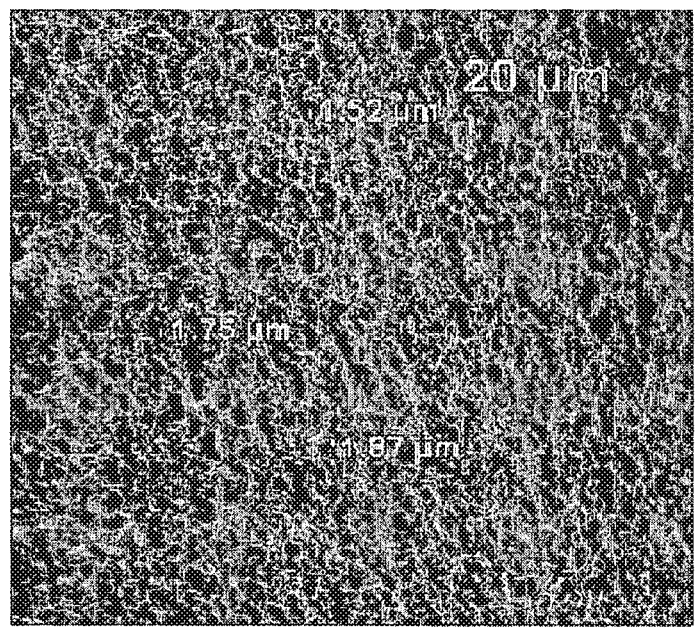

FIGS. 4 A and B report the surfaces produced when the native oxide was removed by the usual method and then the surface was etched with an HCl solution. Although some pitting occurred, it was evident that HCl alone was not sufficient to produce a surface like that of FIG. 1C.

FIGS. 5 A-D illustrate the improved results that were obtained when small amounts of HF were added to the 20 wt % HCl etching solution. It was concluded that a small amount of HF should be used if the desired surface topography was to be obtained. The surfaces of FIGS. 5C and 5D were given the same treatment and produced substantially the same surface, even though the C and D samples had different machining and heats. Thus, it was concluded that the process was broadly applicable to Ti 6/4 alloys.

In the presently preferred process, Ti 6/4 alloy is immersed in an aqueous solution of hydrofluoric acid for the length of time required to remove the native oxide while not removing a significant amount of metal. A preferred solution, suitable for commercial application would contain about 7.9 to 9.0 wt % HF. However, more or less concentrated solutions could be used, with appropriate adjustment of the exposure time, provided that the native oxide was removed to prepare the surface for subsequent etching needed to create the desired surface topography.

The etching step immerses the Ti 6/4 alloy, from which the native oxide had been removed, in an aqueous solution at room temperature containing about 0.053 to 0.105 wt % HF and 19-21 wt % HCl. Such solutions have been found to produce the desired surface topography on Ti 6/4 alloy within about 20 minutes and using only ambient temperatures. Again, some adjustment of the acid concentrations, temperature, and exposure time is believed to be possible, while still obtaining the desired surface. It is believed that equivalent results may be obtained within the broader range of 0.005 to 1.0 wt % HF and 10-30 wt % HCl.

Dental Implants

Figure 6:
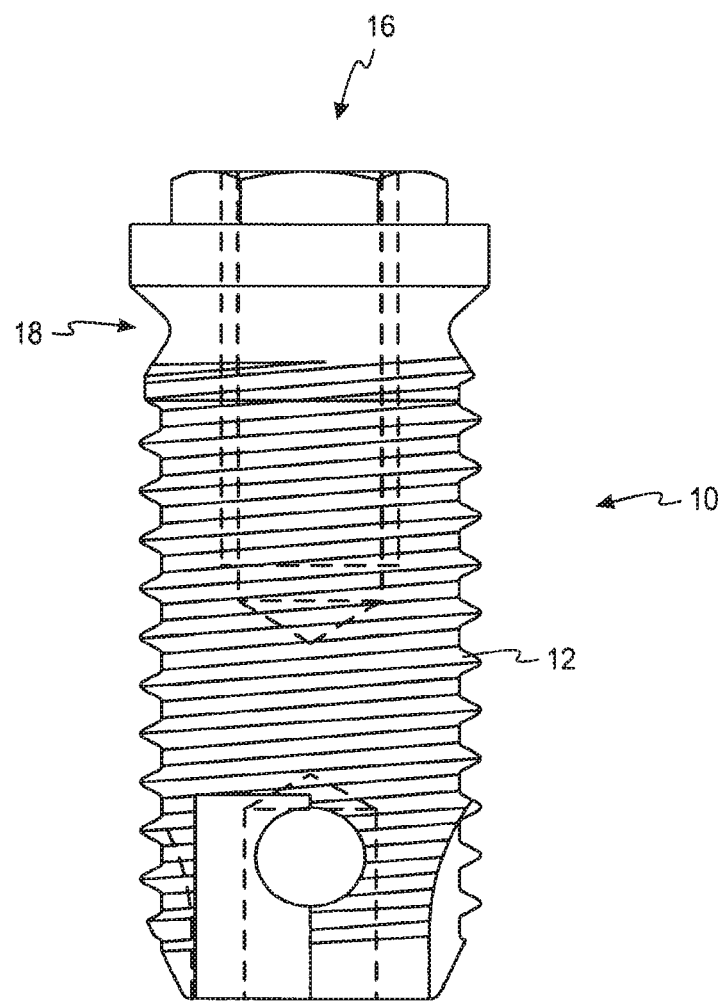
FIG. 6 shows a typical dental implant.

The etching process of the invention may be used to prepare the surface of various styles of dental implants. A typical example is illustrated in FIG. 6. The implant 10 will be placed in a pre-drilled hole in a patient's bone to replace the root of a missing tooth. The threaded portion 12 engages the bone, while at least some of the upper portion 14 contacts tissue. In many cases, the etching process will be applied to the threaded portion 12 of the implant 10, while the upper portion. 14, shown in FIG. 6 to include a head 16 portion for engaging dental prosthesis components and a neck portion 18, remains relatively smooth. In some cases, the roughened area may be extended upward into the neck and head regions, or even to the top of the implant 10. In other cases, only a portion of the threads will be roughened to improve osseointegration of the metal with bone, while the upper section of the threaded region will remain relatively smooth.

What is claimed is:

1. A method of producing a uniformly roughened surface on Ti 6/4 alloy for contact with living bone comprising:
    (a) removing the native oxide from said Ti 6/4 alloy to expose metal;
    (b) contacting said exposed metal with an aqueous solution of 0.005 to 1.0 wt % hydrofluoric acid and 10 to 30 wt % hydrochloric acid for a first period of time to create the desired surface topography having irregularities with peak-to-valley heights of less than 10 microns and average peak-to-peak distance of 1 to 3 microns.

2. The method of claim 1, wherein the first period of time is about 20 minutes.

3. The method of claim 1, wherein the aqueous solution includes 0.084 wt % hydrofluoric acid and about 20 wt % hydrochloric acid.

4. The method of claim 1, wherein the native oxide is removed by contacting the Ti 6/4 alloy with a second aqueous solution of hydrofluoric acid for a second period of time.

5. The method of claim 4, wherein the second aqueous solution contains about 7.9 to 9.0 wt % hydrofluoric acid.

6. The method of claim 5, wherein the second aqueous solution contains about 8.45 wt % hydrofluoric acid.

7. A method of producing a uniformly roughened surface on an implant formed of Ti 6/4 alloy for contact with living bone comprising:
    treating least a portion of an implant surface with a first aqueous solution including hydrofluoric acid for a first period of time to remove native oxide from the implant surface to create a first surface; and
    contacting the first surface with a second aqueous solution including hydrofluoric acid and hydrochloric acid for about twenty (20) minutes at ambient temperature to create a second surface having a topography for osseointegration of the implant with living bone, the topography having peak-to-valley heights of less than 10 microns and average peak-to-peak distance of 1 to 3 microns.

8. The method of claim 7, wherein the first aqueous solution contains about 7.9 to 9.0 wt % hydrofluoric acid.

9. The method of claim 7, wherein the second aqueous solution includes about 0.005 to about 1.0 wt % hydrofluoric acid and about 10 to about 30 wt % hydrochloric acid.

* * * * *